(12) United States Patent
Beck et al.

(10) Patent No.: US 10,105,184 B2
(45) Date of Patent: *Oct. 23, 2018

(54) LASER TISSUE ABLATION SYSTEM

(71) Applicant: Boston Scientific Scimed, Inc., Maple Grove, MN (US)

(72) Inventors: Michael T. Beck, Prior Lake, MN (US); Edouard A. Koullick, Golden Valley, MN (US); Robert E. Lund, Saint Michael, MN (US); Douglas L. Evans, Andover, MN (US); Samuel L. Will, Shell Lake, WI (US); Stuart F. Watson, Mesa, AZ (US); Hyun Wook Kang, Nam-gu (KR); Justin M. Crank, Maple Grove, MN (US); Somany Dy, Cottage Grove, MN (US); Micah D. Thorson, North Branch, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 23 days.

This patent is subject to a terminal disclaimer.

(21) Appl. No.: 15/209,120

(22) Filed: Jul. 13, 2016

(65) Prior Publication Data

US 2017/0007326 A1 Jan. 12, 2017

Related U.S. Application Data

(63) Continuation of application No. 14/521,831, filed on Oct. 23, 2014, now Pat. No. 9,433,467, which is a (Continued)

(51) Int. Cl.
*A61B 18/18* (2006.01)
*A61B 18/24* (2006.01)
(Continued)

(52) U.S. Cl.
CPC .............. *A61B 18/24* (2013.01); *A61B 18/22* (2013.01); *A61B 2017/4216* (2013.01); (Continued)

(58) Field of Classification Search
CPC ........................ A61B 18/24; A61B 2017/4216
(Continued)

(56) References Cited

U.S. PATENT DOCUMENTS 4,976,710 A * 12/1990 Mackin .............. A61B 1/00082
604/916
4,998,930 A * 3/1991 Lundahl ................ A61N 5/062
606/15

(Continued)

OTHER PUBLICATIONS

Non-Final Office Action related to U.S. Appl. No. 13/330,038, dated Feb. 27, 2014.
(Continued)

*Primary Examiner* — John R Downey
(74) *Attorney, Agent, or Firm* — Bookoff McAndrews, PLLC

(57) ABSTRACT

Embodiments of the invention are directed to a laser ablation system. In one embodiment, the laser ablation system comprises a shaft, a balloon, a laser fiber and a viewing fiber. The shaft has a proximal end and a distal end. The balloon is attached to the distal end of the shaft, a portion of which is within the balloon. The laser fiber has a distal end comprising a light dispenser that is configured to deliver laser light through the balloon. The viewing fiber is configured to image an interior balloon. In accordance with another embodiment, the laser ablation system comprises a shaft, a balloon and a laser fiber. The shaft has a proximal end and a distal end. The balloon is attached to the distal end of the shaft, which is within the balloon. The balloon includes an inflated state, in which the balloon is shaped to conform to
(Continued)

a cavity of a patient. The laser fiber has a distal end comprising light dispenser that is configured to deliver laser light through the balloon.

13 Claims, 10 Drawing Sheets

Related U.S. Application Data continuation of application No. 13/152,825, filed on Jun. 3, 2011, now Pat. No. 8,936,592.

(60) Provisional application No. 61/351,127, filed on Jun. 3, 2010.

(51) Int. Cl.
  *A61B 18/22* (2006.01)
  *A61B 17/42* (2006.01)
  *A61B 18/00* (2006.01)
  *A61B 90/00* (2016.01)

(52) U.S. Cl.
  CPC .......... *A61B 2018/0022* (2013.01); *A61B 2018/00196* (2013.01); *A61B 2018/00202* (2013.01); *A61B 2018/00226* (2013.01); *A61B 2018/00559* (2013.01); *A61B 2018/00577* (2013.01); *A61B 2018/00982* (2013.01); *A61B 2018/1861* (2013.01); *A61B 2090/3614* (2016.02)

(58) Field of Classification Search
  USPC .................................. 606/13–15; 607/88–92
  See application file for complete search history.

(56) References Cited

U.S. PATENT DOCUMENTS

| | | |
|---|---|---|
| 5,061,265 A | 10/1991 | Abela et al. |
| 5,074,632 A | 12/1991 | Potter |
| 5,102,402 A | 4/1992 | Dror et al. |
| 5,125,925 A | 6/1992 | Lundahl |
| 5,269,777 A | 12/1993 | Doiron et al. |
| 5,344,419 A * | 9/1994 | Spears ............... A61B 18/245 606/15 |
| 5,409,483 A * | 4/1995 | Campbell ............ A61N 5/0601 606/13 |
| 5,411,016 A | 5/1995 | Kume et al. |
| 5,428,699 A | 6/1995 | Pon |
| 5,431,647 A | 7/1995 | Purcell, Jr. et al. |
| 5,437,660 A * | 8/1995 | Johnson ................ A61B 18/24 606/15 |
| 5,458,595 A | 10/1995 | Tadir et al. |
| 5,530,780 A | 6/1996 | Ohsawa |
| 5,533,508 A | 7/1996 | Doiron |
| 5,569,240 A | 10/1996 | Dowlatshahi et al. |
| 5,593,405 A | 1/1997 | Osypka |
| 5,609,591 A | 3/1997 | Daikuzono |
| 5,645,562 A | 7/1997 | Haan et al. |
| 5,695,583 A | 12/1997 | van den Bergh et al. |
| 5,729,092 A | 3/1998 | Doiron et al. |
| 5,730,700 A | 3/1998 | Walther et al. |
| 5,733,277 A | 3/1998 | Pallarito |
| 5,756,145 A | 5/1998 | Darouiche |
| 5,807,390 A | 9/1998 | Fuller et al. |
| 5,824,005 A | 10/1998 | Motamedi et al. |
| 5,854,422 A | 12/1998 | McKeon et al. |
| 5,876,426 A | 3/1999 | Kume et al. |
| 5,891,082 A | 4/1999 | Leone et al. |
| 5,891,136 A | 4/1999 | McGee et al. |
| 5,911,720 A | 6/1999 | Bourne et al. |
| 5,947,958 A | 9/1999 | Woodard et al. |
| 5,997,571 A | 12/1999 | Farr et al. |
| 6,013,053 A | 1/2000 | Bower et al. |
| 6,027,524 A | 2/2000 | Petit |
| 6,086,558 A | 7/2000 | Bower et al. |
| 6,096,030 A | 8/2000 | Ortiz |
| 6,146,409 A * | 11/2000 | Overholt ............. A61N 5/0601 606/15 |
| 6,270,492 B1 | 8/2001 | Sinofsky |
| 6,391,052 B2 | 5/2002 | Buirge et al. |
| 6,398,779 B1 | 6/2002 | Gu et al. |
| 6,423,055 B1 | 7/2002 | Farr et al. |
| 6,471,692 B1 * | 10/2002 | Eckhouse ............ A61N 5/0601 606/14 |
| 6,482,197 B2 | 11/2002 | Finch et al. |
| 6,500,174 B1 * | 12/2002 | Maguire ............ A61B 18/1492 606/41 |
| 6,514,245 B1 * | 2/2003 | Williams ............... A61B 18/02 128/898 |
| 6,522,806 B1 | 2/2003 | James, IV et al. |
| 6,524,274 B1 | 2/2003 | Rosenthal et al. |
| 6,562,029 B2 | 5/2003 | Maki et al. |
| 6,572,609 B1 | 6/2003 | Farr et al. |
| 6,602,246 B1 * | 8/2003 | Joye ........................ A61B 5/01 606/20 |
| 6,616,653 B2 | 9/2003 | Beyar et al. |
| 6,626,900 B1 | 9/2003 | Sinofsky et al. |
| 6,706,004 B2 | 3/2004 | Tearney et al. |
| 6,708,056 B2 | 3/2004 | Duchon et al. |
| 6,796,972 B1 | 9/2004 | Sinofsky et al. |
| 6,829,411 B2 | 12/2004 | Easley |
| 6,837,885 B2 | 1/2005 | Koblish et al. |
| 6,899,706 B2 | 5/2005 | Siatkine |
| 6,953,457 B2 | 10/2005 | Farr et al. |
| 6,986,764 B2 | 1/2006 | Davenport et al. |
| 7,112,195 B2 | 9/2006 | Boll et al. |
| 7,131,963 B1 | 11/2006 | Hyde |
| 7,135,034 B2 | 11/2006 | Friedman et al. |
| 7,169,140 B1 | 1/2007 | Kume |
| 7,207,984 B2 | 4/2007 | Farr et al. |
| 7,261,730 B2 | 8/2007 | Friedman et al. |
| 7,357,796 B2 | 4/2008 | Farr et al. |
| 7,359,601 B2 * | 4/2008 | Loeb ..................... A61B 18/22 385/116 |
| 7,449,026 B2 | 11/2008 | Zalesky et al. |
| 7,559,925 B2 * | 7/2009 | Goldfarb ............ A61B 1/00126 604/510 |
| 7,905,874 B2 | 3/2011 | Miller et al. |
| 8,016,748 B2 * | 9/2011 | Mourlas ............. A61B 1/00082 600/104 |
| 8,241,273 B2 * | 8/2012 | Whayne ............. A61B 18/1492 128/898 |
| 8,876,807 B2 | 11/2014 | Evans et al. |
| 8,936,592 B2 | 1/2015 | Beck et al. |
| 2002/0013601 A1 * | 1/2002 | Nobles ................... A61B 1/32 606/193 |
| 2002/0045894 A1 * | 4/2002 | Joye ....................... A61B 18/02 606/21 |
| 2002/0161358 A1 * | 10/2002 | Liu ....................... A61B 18/22 606/15 |
| 2002/0183731 A1 * | 12/2002 | Holland ................. A61B 18/02 606/21 |
| 2002/0193850 A1 * | 12/2002 | Selman ............... A61K 41/0057 607/89 |
| 2003/0036752 A1 * | 2/2003 | Joye ...................... A61B 18/02 606/21 |
| 2004/0002749 A1 * | 1/2004 | Joye ................... A61B 1/00082 607/105 |
| 2004/0082859 A1 * | 4/2004 | Schaer .................... A61N 7/02 600/459 |
| 2004/0133254 A1 | 7/2004 | Sterzer et al. |
| 2005/0203496 A1 * | 9/2005 | Ritchie ................... A61B 18/24 606/15 |
| 2005/0255039 A1 | 11/2005 | Desai |
| 2007/0032783 A1 * | 2/2007 | Abboud ................ A61B 18/02 606/21 |
| 2007/0197896 A1 * | 8/2007 | Moll ................... A61B 1/00039 600/407 |
| 2007/0282403 A1 * | 12/2007 | Tearney ................. A61B 18/24 607/89 |

(56) References Cited

U.S. PATENT DOCUMENTS

| | | |
|---|---|---|
| 2008/0039828 A1 | 2/2008 | Jimenez et al. |
| 2008/0281317 A1* | 11/2008 | Gobel .................... A61B 18/04 606/41 |
| 2009/0138000 A1* | 5/2009 | Vancelette ............. A61B 18/02 606/21 |
| 2010/0298757 A1 | 11/2010 | Frigstad |
| 2011/0301584 A1 | 12/2011 | Beck et al. |
| 2012/0157981 A1 | 6/2012 | Evans et al. |

OTHER PUBLICATIONS

Final Office Action related to U.S. Appl. No. 13/152,825, dated May 28, 2014.
Non-Final Office Action related to U.S. Appl. No. 13/330,038, dated Nov. 8, 2013.
Non-Final Office Action related to U.S. Appl. No. 13/330,038, dated Aug. 12, 2013.
Non-Final Office Action related to U.S. Appl. No. 13/152,825, dated May 8, 2013.
U.S. Appl. No. 12/468,668, filed May 19, 2009.
Pietrafitta, Joseph J., MD, "Laser Therapy of Cancer of the Gastrointestinal and Biliary Tracts", Seminars in Surgical Oncology 5:17-29, 1989.

\* cited by examiner

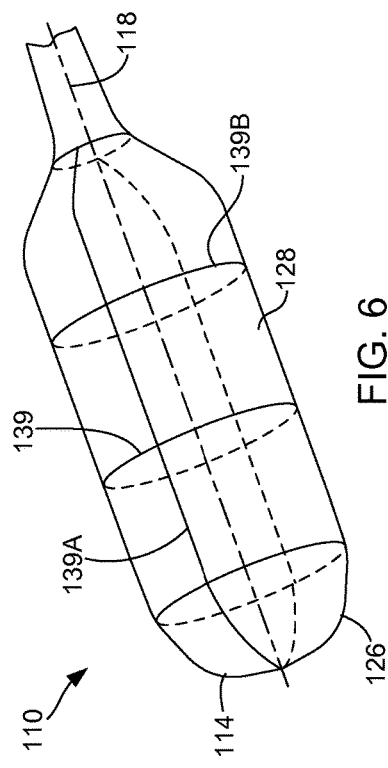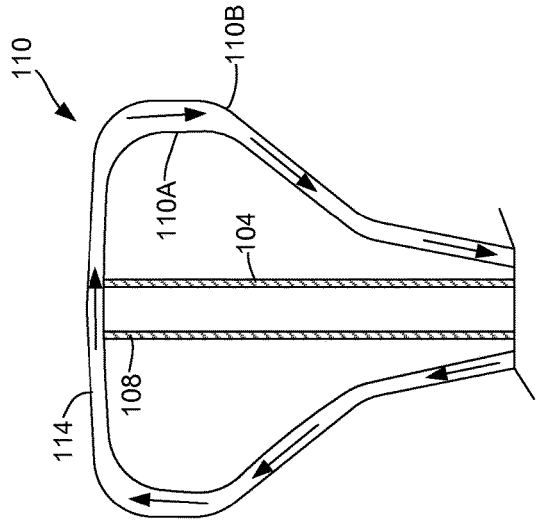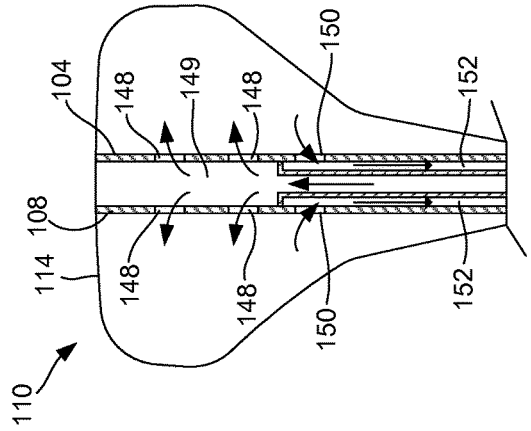

LASER TISSUE ABLATION SYSTEM

CROSS-REFERENCE TO RELATED APPLICATION

This application is a continuation of U.S. application Ser. No. 14/521,831, filed Oct. 23, 2014, now U.S. Pat. No. 9,433,467, which is a continuation of U.S. application Ser. No. 13/152,825, filed Jun. 3, 2011, now U.S. Pat. No. 8,936,592, which claims the benefit of U.S. Provisional Application No. 61/351,127, filed Jun. 3, 2010. The contents of all off the above-referenced applications are herein incorporated by reference in their entirety.

BACKGROUND OF THE INVENTION

Pelvic conditions include diseases of the uterus, such as uterine fibroids and menorrhagia. Uterine fibroids are non-cancerous tumors of the uterus that typically appear on the endometrium layer (i.e., uterine wall) of the uterus. Menorrhagia is a medical condition involving excessive and difficult to control bleeding of the endometrial layer of the uterus. These conditions have been treated through hysterectomy. However, alternative, less radical approaches are also being used.

One alternative to a hysterectomy is endometrial ablation, which induces necrosis of the endometrial layer and a portion of the myometrial layer. These treatments can include freezing and heating the endometrial layer, or cauterizing the endometrial layer using a laser.

SUMMARY

Some embodiments of the invention are directed to a laser ablation system. In one embodiment, the laser ablation system comprises a shaft, a balloon, a laser fiber and a viewing fiber. The shaft has a proximal end and a distal end. The balloon is attached to the distal end of the shaft, a portion of which is within the balloon. The laser fiber has a distal end comprising a light dispenser that is configured to deliver laser light through the balloon. The viewing fiber is configured to image an interior balloon.

In accordance with another embodiment, the laser ablation system comprises a shaft, a balloon and a laser fiber. The shaft has a proximal end and a distal end. The balloon is attached to the distal end of the shaft, which is within the balloon. The balloon includes an inflated state, in which the balloon is shaped to conform to a cavity of a patient. The laser fiber has a distal end comprising light dispenser that is configured to deliver laser light through the balloon.

Additional embodiments are directed to a method a using the laser ablation system. In one embodiment, a laser ablation system is provided that comprises a shaft, a balloon and a laser fiber. The shaft has a proximal end and a distal end. The balloon is attached to the distal end of the shaft, which is within the balloon. The balloon includes an inflated state, in which the balloon is shaped to conform to a uterine cavity of a patient. The laser fiber has a distal end comprising a light dispenser that is configured to deliver laser light through the balloon. Also in the method, the distal end of the shaft is fed into the uterus of a patient with the balloon in a deflated state. The balloon is inflated with a gas or fluid to the inflated state, in which the balloon substantially conforms to the uterine cavity of the patient and engages the uterine walls. Laser light is then transmitted through the laser fiber and, the light dispenser and the balloon. The tissue of the uterine walls is ablated responsive to the transmission of the laser light.

BRIEF DESCRIPTION OF THE DRAWINGS

FIG. 6 is an isometric view of a balloon in accordance with embodiments of the invention.

FIGS. 7 and 8 are side cross-sectional views of a distal end of an applicator illustrating fluid or gas flow in accordance with embodiments of the invention.

DETAILED DESCRIPTION OF ILLUSTRATIVE EMBODIMENTS

Embodiments of the present invention are directed to a laser tissue ablation system designed to perform tissue ablation and/or other laser treatments on a patient. While particular embodiments of the invention will be described as useful in treating menorrhagia through endometrial ablation of the uterine wall of a patient, those skilled in the art understand that the system of a present invention may be adapted to perform ablation treatments of other tissue of a patient, such as that of the anal cavity, the bladder, the vagina, the esophagus, the trachea, the urethra, the ureter, the prostate gland, the kidney, intestinal growths or abnormal tissues of the intestine (e.g., hemorrhoids, polyps, etc.) and cancerous tissues.

Figure 1:
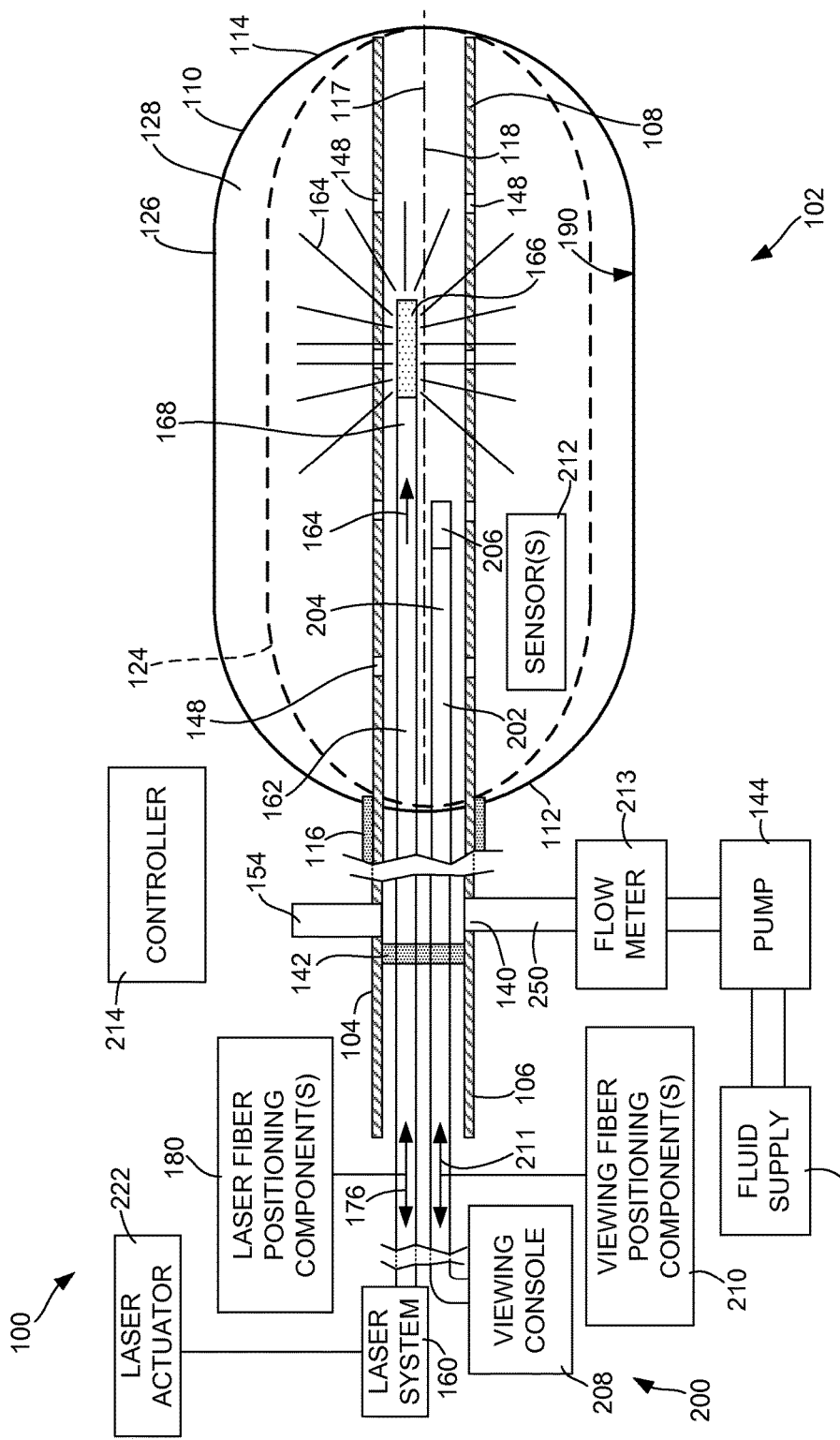
FIG. 1 is a simplified diagram of a laser tissue ablation system formed in accordance with embodiments of the invention.

FIG. 1 is a simplified diagram of a laser tissue ablation system 100 formed in accordance with embodiments of the invention. One embodiment of the system 100 includes an applicator 102 that is formed in accordance with the embodiments described below.

One embodiment of the applicator 102 comprises a shaft 104 having a proximal end 106 and a distal end 108. One embodiment of the shaft 104 is formed of a rigid and substantially transparent material, such as, for example, acrylic, PET, silicone, polyurethane, polycarbonate, glass or other suitable material. In one embodiment, the applicator 102 includes a balloon 110 that is attached to the shaft 104 proximate the distal end 108. In one embodiment, the balloon 110 comprises a proximal end 112 and a distal end 114. In one embodiment, the proximal end 112 is attached to the shaft 104 by a sleeve 116 that is formed, for example out of Teflon®, which seals an opening of the balloon 110 to the shaft 104.

In one embodiment, the distal end 108 of the shaft 104 is attached to the distal end 114 of the balloon 110. In one embodiment, the shaft 104 has a longitudinal axis 117. In one embodiment, the distal end 108 of the shaft 104 is secured to the distal end 114 of the balloon 110 along longitudinal axis 117. In one embodiment, the longitudinal axis 117 is aligned with a central axis 118 of the balloon 110. In one embodiment, the balloon is symmetric about the longitudinal or central axis 117 when inflated.

Figure 2:
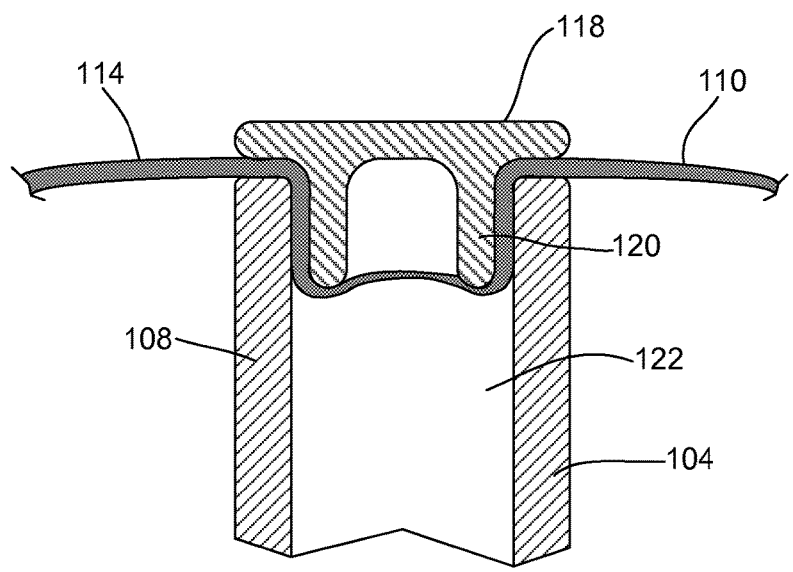
FIG. 2 is a cross-sectional view illustrating the attachment of a distal end of a shaft to a balloon, in accordance with an exemplary embodiment.

The attachment of the balloon 110 to the shaft 104 can be accomplished in many different ways. FIG. 2 is a cross-sectional view illustrating an exemplary means of attaching the shaft 104 to the balloon 110 using a cap 119. The cap 119 comprises a cylindrical portion 120 that is received within a bore 122 of the shaft 104. The distal end 114 of the balloon 110 is captured between the surfaces of the cylindrical portion 120 of the cap 119 and the shaft 104. In one embodiment, frictional resistance prevents the cap 119 from becoming dislodged from the bore 122 of the shaft 104. A biocompatible adhesive may also be used to secure the cap 119 to the distal end 108 of the shaft 104. Other techniques may also be used to secure the balloon 110 to the distal end 108 of the shaft 104.

The balloon 110 has deflated and inflated states. The deflated state 124 of the balloon 110 is preferably sufficiently compact to allow the distal end 108 of the shaft 104 and the attached balloon 110 to be inserted into the desired cavity of the patient, such as the uterus or vagina, to locate the balloon 110 proximate the tissue targeted for treatment. In one embodiment, the deflated state of the balloon 110 is approximately 4-6 mm or less in diameter measured radially from the central axis 118 of the balloon 110. When in the inflated state, the balloon 110 substantially conforms to the cavity in which it is placed.

In one embodiment, the balloon 110 is be formed of a suitable biocompatible material. In one embodiment, the balloon 110 is formed of a distensible material, such as silicone, PET, polyurethane, rubber or other suitable material. The distensible material can stretch responsive to inflating the balloon 110 from a deflated state 124 (illustrated in phantom in FIG. 1) to an inflated state 126 (solid line), as shown in FIG. 1, due to an increase in the pressure of the interior 128 of the balloon 110. The distensible material allows the balloon 110 to further conform to the cavity of the patient in which it is placed in response to pressure exerted on the balloon 110 from the walls of the cavity.

In accordance with another embodiment, the balloon 110 is formed of minimally distensible material, such as polyurethane, or other suitable material.

In one embodiment, the balloon 110 includes an Inhibizone coating, such as that described in U.S. Pat. No. 5,756,145, which is incorporated herein by reference in its entirety.

Figure 3:
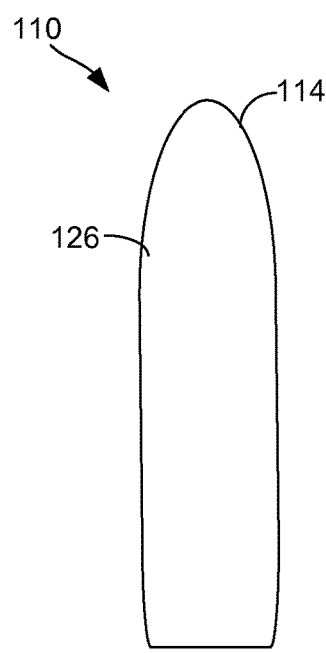
FIGS. 3 and 4 are simplified diagrams of inflated balloons in accordance with embodiments of the invention.
Figure 4:
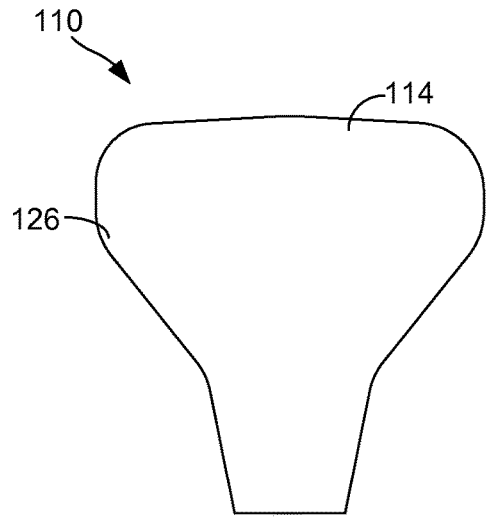

FIGS. 3 and 4 are simplified diagrams of the balloon 110 in the inflated state 126, in accordance with embodiments of the invention. In one embodiment, the inflated state 126 of the balloon 110 has a cylindrical shape with a rounded distal end 114, as illustrated in FIGS. 1 and 3.

In accordance with another embodiment, the inflated state 126 of the balloon 110 has a predefined non-cylindrical or spherical shape when viewed in a plane aligned with the central axis of the balloon 117. Rather, the inflated state 126 of the balloon has a shape that conforms to the interior cavity of the patient where the tissue targeted for ablation is located. One exemplary embodiment is illustrated in the simplified side view of FIG. 4, in which the inflated state 126 of the balloon 110 is shaped to conform to the uterus of a patient. The balloon 110 can take on other cavity-conforming shapes, such as the vagina, the anal cavity, esophagus, trachea, bladder and any other cavity within the body.

When the balloon 110 is formed of substantially non-distensible material, the predefined inflated shape 126 of the balloon 110 will drive the tissue of the cavity into conformity with the balloon 110. When the balloon 110 is formed distensible material, the inflated state 126 of the balloon will generally conform to the cavity of the patient. As a result, the balloon 110 may only minimally deflect the walls of the cavity when the balloon is inflated. Further, the balloon 110 will also deform in response to engagement with the walls of the cavity.

In one embodiment, the pre-defined shape of the inflated state 126 of the balloon prevents the balloon from applying significant pressures to the walls of the cavity of the patient. In one embodiment, the balloon 110 applies less than 10 psi to the walls of the cavity of the patient in which it is inflated. Thus, the balloon 110 having a pre-defined inflated shape can significantly reduce the pressure on the walls of the cavity of the patient in which the balloon 110 is inflated. This can reduce patient intraoperative and post operative pain.

Figure 5:
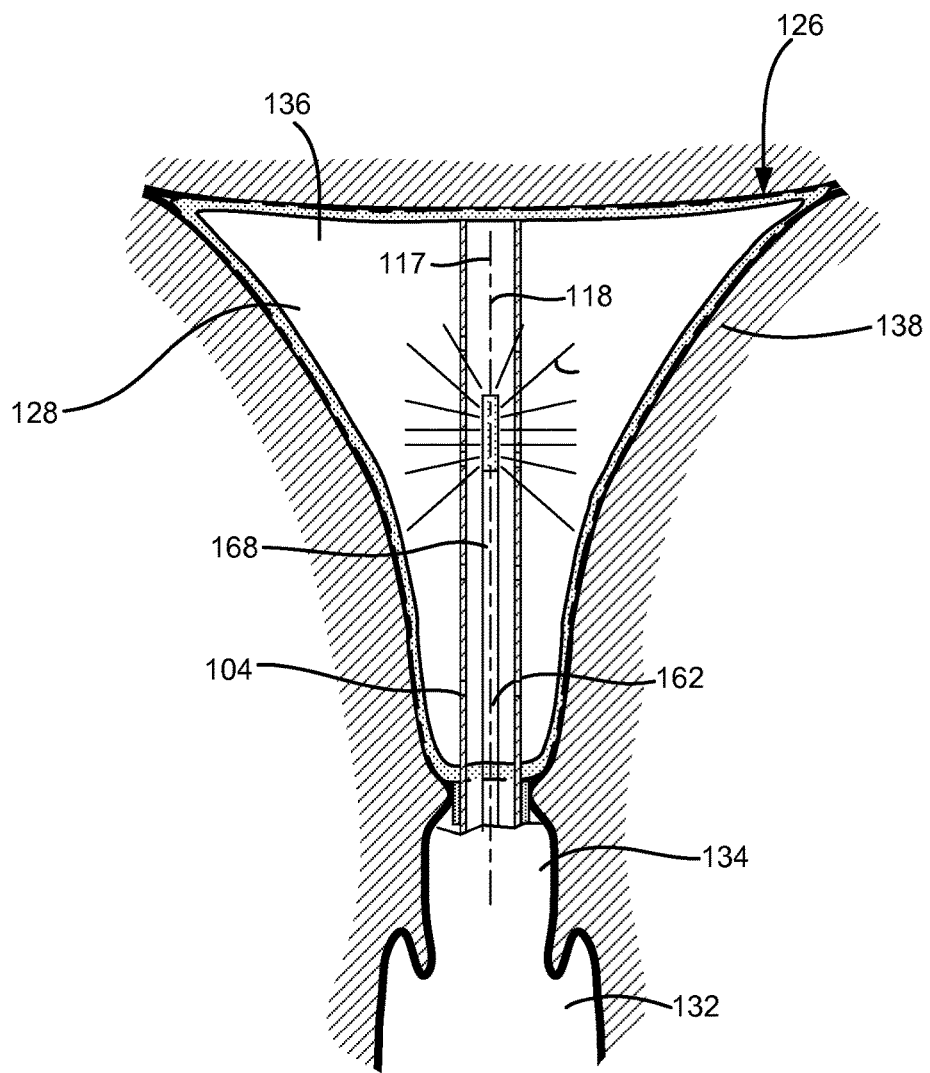
FIG. 5 is a cross-sectional view depicting pelvic anatomy of a female patient and a distal end of the applicator formed in accordance with embodiments of the invention.

FIG. 5 is a cross-sectional view of a female patient depicting the vagina 132, the cervix 134 and the uterus 136. The distal end 108 of the shaft 104 and a balloon 110 are inserted through the cervix 134 and into the uterus 136 when the balloon 110 is in the deflated state 124. The balloon 110 is then expanded to the inflated state 126 (shown), in which the balloon 110 substantially conforms to the shape of the uterine wall 138. The balloon 110 preferably engages the uterine wall 138 while applying minimal pressure. In one embodiment, the balloon 110 applies less than 10 psi to the uterine wall 138 when in the inflated state 126.

In one embodiment, the balloon 110 includes markings 139, as shown in FIG. 6. The markings 139 can be viewed from within the interior 128 to determine whether the balloon 110 is properly inflated and/or positioned within the cavity of the patient. In one embodiment, the markings 139 comprise one or more visible lines extending longitudinally (i.e., lines 139A), and/or circumferentially (i.e., lines 139B) around the balloon 110. In one embodiment, the markings 139 comprise a grid pattern.

In one embodiment, the balloon 110 seals the distal end 108 of the shaft 104. A seal 142, such as an o-ring, or other suitable seal, seals the proximal end 106 of the shaft 104. In one embodiment, the balloon 110 is inflated using a simple saline solution.

In one embodiment, the balloon 110 may be inflated with fluid or gas. In one embodiment, the shaft 104 includes a port 140, as shown in FIG. 1, through which the fluid or gas may be received. In one embodiment, the system 100 comprises a pump 144 that drives a fluid or gas from a supply 146 through the port 140 and into the interior 128 of the balloon 110 to drive the balloon 110 to its inflated state 126. The pump 144 can take on many different forms. In one embodiment, the supply 146 is in the form of a pressurized gas, in which case, the pump 144 may represent a valve that controls the flow of the gas from the supply 146. In accordance with another embodiment, the pump 144 drives a fluid from the supply 146 through the port 140 and into the interior 128 of the balloon 110 to inflate the balloon 110. Embodiments of the pump 144 include a syringe, a diaphragm pump, gear pump, or other suitable pump.

In one embodiment, gas or fluid enters the shaft 104 through the port 140, shown in FIG. 1. In one embodiment, the shaft 104 includes a fluid path 149 that fluidically couples the port 140 to openings 148 in the shaft 104 to the interior 128 of the balloon 110, as shown in FIG. 7. The gas or fluid entering the port 140 flows through the fluid path 149, through the openings 148 and into the interior 128 of the balloon 110 as shown in FIGS. 1 and 7. In accordance with one embodiment, the fluid or gas within the interior cavity 128 of the balloon 110 may be discharged back through the openings 148 of the shaft 104 and out the port 140. Alternatively, as shown in FIG. 7, the fluid or gas within the interior cavity 128 of the balloon 110 may be discharged through one or more openings 150 to a fluid path 152 that is connected to a dedicated drain port 154 (FIG. 1).

In accordance with one embodiment, the balloon 110 comprises an interior balloon 110A and an exterior balloon 110B, as shown in the simplified side-cross sectional view of FIG. 8. In accordance with one embodiment, either the interior balloon 110A or the exterior balloon 110B is formed of a non-distensible material, while the other balloon 110A or 110B is formed of a distensible material. In one embodiment, the interior balloon 110A is formed of a substantially non-distensible or minimally distensible material and has a predefined shaped in accordance with embodiments described above. In accordance with one embodiment, a biocompatible lubricant is located between the interior balloon 110A and the exterior balloon 110B.

In accordance with one embodiment, the fluid or gas driven through the port 140 is fed between the interior balloon 110A and the exterior balloon 110B, as represented by the arrows in FIG. 8. In one embodiment, the fluid is discharged through the fluid path 152 and out the drain port 154. The flow of fluid between the balloons 110A and 110B can be used to control the temperature of the tissue that is in contact with the balloon 110B.

One embodiment of the system 100 includes a conventional laser source 160 that can be attached to a waveguide 162, such as an optical fiber (hereinafter "laser fiber"), that can be received within the shaft 104. The laser source 160 can be a conventional laser generating system. In accordance with one embodiment, the laser source 160 is configured to generate laser light or a laser 164 having a desired wavelength for performing surgical procedures, such as tissue ablation.

In one embodiment, the laser source 160 is configured to produce an Nd:YAG laser operating at approximately 532 nanometers or 1064 nanometer wavelengths. The laser source 160 may be a solid state laser based on a potassium-titanyl-phosphate (KTP) crystal, a lithium triborate (LBO) laser, a beta barium borate (BBO), a holmium laser and a thulium laser, or other type of laser source used to perform tissue ablation or other laser treatment. Exemplary laser sources 160 are described in U.S. Pat. No. 6,986,764 (Davenport), which is incorporated herein by reference in its entirety.

The laser 164 generated by the laser source 160 travels through the laser fiber 162 and is discharged through a light dispenser 166 at a distal end 168. In one embodiment, the dispensed laser light 164 is transmitted through the shaft 104 and the balloon 110 and onto the targeted tissue of the patient, such as the uterine wall 138 shown in FIG. 5.

The light dispenser 166 is configured to discharge the laser light 164 in a desired manner, such as along the axial and/or radial directions of the laser fiber 162, to one side of the laser fiber 162, in a diffuse pattern around the dispenser 166, and/or other desired manner. Exemplary light dispensers 166, such as side-fire optical caps, are disclosed in U.S. Pat. No. 5,428,699 (Pon), U.S. Pat. No. 5,269,777 (Doiron et al.), U.S. Pat. No. 5,530,780 (Ohsawa), and U.S. Pat. No. 5,807,390 (Fuller et al.).

Figure 9:
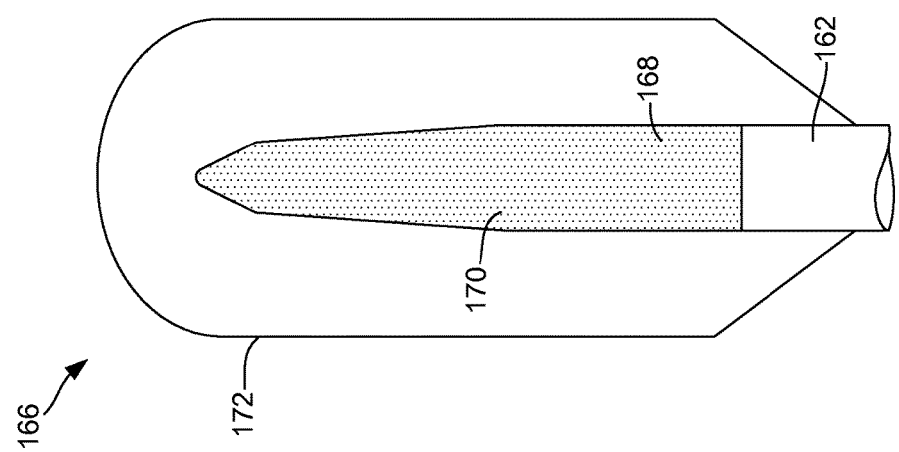

In one embodiment, the light dispenser 166 comprises an etched section 170 of the laser fiber 162, as shown in FIG. 9, to dispense the laser light 164 in a diffuse pattern. In one embodiment, portions of the etched section 170 are tapered to direct the diffused laser light in a desired manner, such as axially. The etching can be made using an appropriate laser, such as a $CO_2$ laser, to roughen the exterior surface of the laser fiber 162. In one embodiment, a cap 172 encloses the dispenser 166, as shown in FIG. 9.

If the laser light 164 is output from the dispenser 166 in an even dispersion pattern, the targeted tissue located farther away will receive less laser light energy than the targeted tissue located closer to the dispenser 166. In one embodiment, the etching pattern of the section 170 is customized to include portions that transmit more light energy than other portions to customize the laser energy dispersion pattern output from the dispenser 166. That is, the etched section 170 may comprise different patterns in different portions of the section 170 to provide different levels of laser light transmission through the different portions of the section 170. This allows the targeted tissue to receive similar intensity levels of the dispensed laser light 164 even though the targeted tissue is not located a uniform distance from the dispenser 166.

In accordance with one embodiment, light transmission through the balloon 110 is non-uniform. In one embodiment, light transmission through the balloon varies along the central axis 118 of the balloon 110. That is, portions of the balloon 110 at different locations along the axis 118 (e.g., portions in a plane that is perpendicular to the axis 118) have a degree of laser transparency that is different from other portions of the balloon along the axis 118. This allows for the control of the transmission of the laser light 164 through the balloon 110 and, therefore, the amount of laser energy that is delivered to the targeted tissue.

In one embodiment, the material forming the balloon provides a predefined pattern of laser transparency variation along the axis 118, such as, for example, by varying a thickness of the balloon 110. In one embodiment, printing or a coating of material on of the balloon 110, such as on the interior wall 190 (FIG. 1), defines the desired pattern of laser transparency though the balloon 110. In one embodiment, the printing or coating defines the pattern of laser transparency by applying the printing or coating to select portions of the balloon 110, applying the printing or coating in a varying pattern on the balloon 110, and/or applying the printing or coating in a varying thickness on the balloon 110. Embodiments of the coating may comprise titanium dioxide ($TiO_2$), Tampapur Ink, and/or parylene. In one embodiment, the coated or printed material is reflective.

Figure 10:
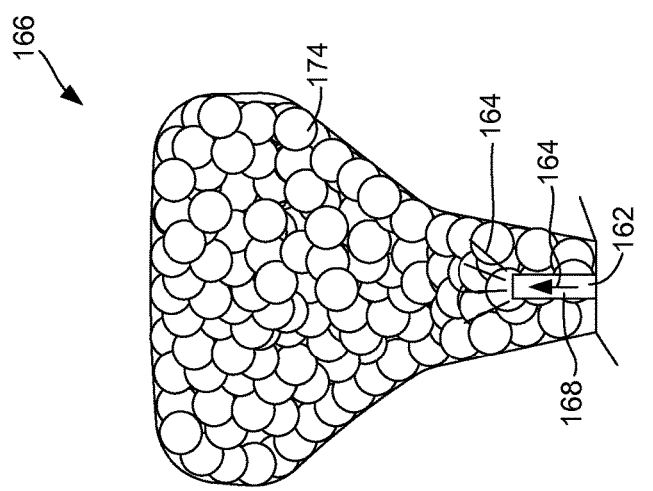
FIGS. 9 and 10 are side views of light dispensers in accordance with embodiments of the invention.

FIG. 10 illustrates a simplified diagram of a light dispenser 166 in accordance with another embodiment of the invention. In accordance with this embodiment, the light dispenser 166 comprises a plurality of glass beads 174 within the balloon 110. The laser light is discharged through the distal end 168 of the laser fiber 162 and interacts with the glass beads 174 to disperse the laser light 164 around the surface of the balloon 110.

In one embodiment, the distal end 108 of the shaft 104 is configured to transmit the laser light 164 discharged through the dispenser 166 of the laser fiber 162 at varying degrees of efficiency. That is, sections of the shaft 104 are configured to be more transparent to the laser light 164 than other sections of the shaft 104. This pattern of laser transparency of the shaft may be formed in various ways. In one embodiment, the interior or exterior wall of the shaft 104 is coated as described above with regard to the balloon 110. Alternatively, the pattern may be formed on the shaft 104 by etching the pattern on the shaft 104, applying a particulate to the shaft 104 that blocks the laser light 164, tinting the shaft 104, or other suitable technique for creating the desired pattern of laser transparency through the shaft 104. As discussed above with regard to the dispenser 166 illustrated in FIG. 9, the control of the transmission of the laser light 164 through the shaft 104 provides control over the amount of laser energy that is delivered to the targeted tissue.

One embodiment of the system 100 includes one or more laser fiber positioning components 180 represented schematically in FIG. 1. In one embodiment, the positioning components 180 are configured to move the laser fiber 162 axially along the longitudinal axis of the laser fiber, as indicated by arrow 176 in FIG. 1, relative to the shaft 104 and/or the balloon 110. This axial movement of the distal end 168 laser fiber 162 causes the laser fiber 162 to generally move along the longitudinal axis 117 of the shaft 104 and along the central axis 118 of the balloon 110 relative to the balloon 110 and the shaft 104. In accordance with one embodiment, the distal end 168 of the laser fiber 162 may be moved axially by the one or more components 180 to withdraw the distal end 168 and the dispenser 166 of the laser fiber 162 from within the interior 128 of the balloon 110. The components 180 may also move the distal end 168 and the dispenser 166 of the laser fiber 162 into the interior 128 of the balloon 110. Thus, the dispenser 166 of the laser fiber 162 may be positioned in the desired location relative to the balloon 110 and the shaft 104 using the one or more laser fiber positioning components 180.

In accordance with another embodiment, the laser fiber positioning components 180 are configured to rotate the laser fiber 162 about its longitudinal axis and, thus, rotate (i.e., move angularly) the dispenser 166 about the longitudinal axis. This may be useful when the dispenser 166 is configured to output the laser light 164 radially out a side of the dispenser 166 over a range of less than 360°. With such a configuration, the dispenser 166 can be made to output the laser light 164 to the tissue surrounding the dispenser 166 by rotating the dispenser 360° using the positioning components 180.

Figure 11:
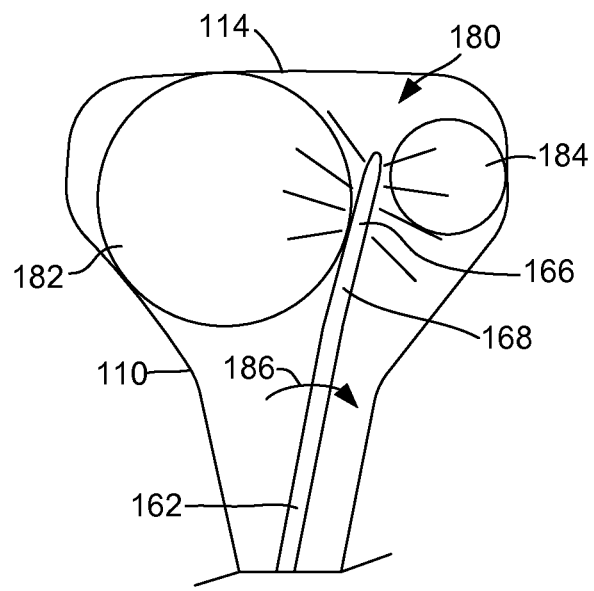
FIGS. 11 and 12 are side views of the distal end of the applicator illustrating laser fiber positioning components in accordance with embodiments of the invention.
Figure 12:
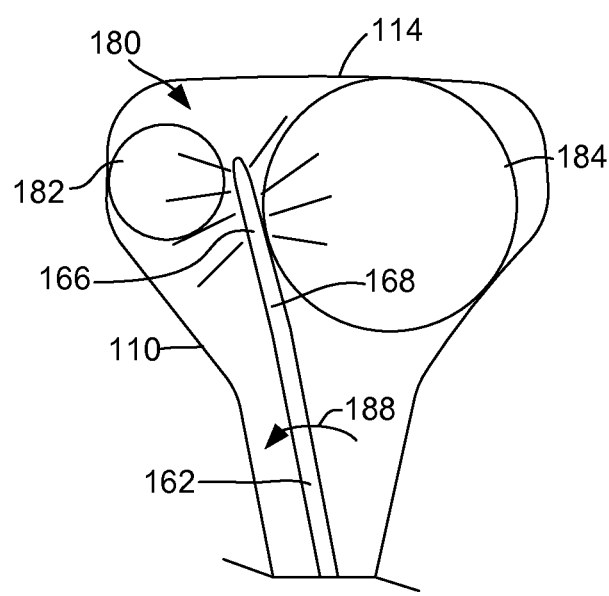

In accordance with one embodiment, the one or more positioning components 180 are configured to move the distal end 168 of the laser fiber 162 in an arc relative to the balloon 110. FIGS. 11 and 12 illustrate exemplary components 180 for moving the distal end of the laser fiber 162 in an arc. In one embodiment, the components 180 comprise at least two balloons 182 and 184 that may be inflated and deflated through the pumping of a gas or fluid through suitable conduit (not shown) coupled to the balloons 182 and 184. In one embodiment, the distal end 168 of the laser fiber 162 is not covered by the shaft 104. Movement of the distal end 168 of the laser fiber 162 along an arc in the direction indicated by arrow 186 is accomplished by deflating the balloon 184 and inflating the balloon 182, as shown in FIG. 11. Likewise, the distal end 168 of the laser fiber 162 may be moved in an arc in the direction indicated by arrow 188 by deflating the balloon 182 and inflating the balloon 184, as shown in FIG. 12. Additional balloons may be used in a similar manner to displace the distal end 168 of the laser fiber 162 along an arc in the desired direction.

One embodiment of the system 100 includes a viewing system 200 that is configured to provide the physician with a view from the interior 128 of the balloon 110. One embodiment of the viewing system 200 comprises a viewing fiber 202 that is received within the shaft 104, as shown in FIG. 1. In one embodiment, the distal end 204 comprises an imaging component 206, such as a charge coupled device (CCD) that is configured to image the interior 128 of the balloon 110 through the shaft 104. The imaging component 206 may be a conventional device that includes the necessary electronics to deliver the image data down the viewing fiber 202 to a suitable viewing console 208 through one or more wires (not shown). A capsule or other protective means can protect the imaging component 206 from the environment within the interior 128 of the balloon 110.

In one embodiment, the viewing system 200 includes one or more viewing fiber positioning components 210 that are configured to adjust the position and/or orientation of the imaging component 206 to image the desired portion of the balloon 110 or the targeted tissue of the patient. In one embodiment, the positioning components 210 are configured to move the viewing fiber 202 axially along the longitudinal axis of the viewing fiber, as indicated by arrow 211 in FIG. 1 relative to the shaft 104 and/or the balloon 110. Accordingly, the distal end 204 of the viewing fiber 202 may be moved axially by the one or more components 210 to withdraw the imaging component 206 from within the interior 128 of the balloon 110. The imaging component 206 can be moved from this withdrawn position into the interior 128 of the balloon 110 and positioned in a desired location relative to the balloon 110 and the shaft 104. In accordance with another embodiment, the viewing fiber positioning components 210 are configured to rotate the viewing fiber 202 about its longitudinal axis and, thus, rotate the imaging component 206 about the longitudinal axis of the viewing fiber 202. This allows the imaging component 206 to image a full 360° around the longitudinal axis of the viewing fiber 202.

Exemplary positioning components for the laser fiber 162 and the components 210 for the viewing fiber 202 include components that facilitate the hand feeding of the fibers 162 and 202, and components that drive the feeding of the laser fiber 162 and the viewing fiber 202, such as rollers that are rotated by hand or driven by a motor, or other suitable mechanism for feeding the laser fiber 162 and the viewing fiber 202 in their axial directions. In one embodiment, the components 180 and 210 are configured to rotate the laser fiber 162 and the viewing fiber 202, respectively, and include components that facilitate the rotation of the fibers by hand, mechanisms that are driven by hand or by a motor that engage the fibers and rotate the fibers about their longitudinal axis, or other components that can be used to rotate the fibers.

Another embodiment of the system 100 includes one or more sensors 212 (FIG. 1) that are configured to sense a parameter of the system 100 and/or the patient. One embodiment of the sensors includes a temperature sensor, such as a thermal couple, that is configured to sense the temperature of the balloon 110 and/or the tissue of the patient. In accordance with one embodiment, when the balloon 110 comprises and internal balloon 110A and an external balloon 110B (FIG. 8), the temperature sensor is located between the balloons 110A and 110B. In accordance with another embodiment, the sensors 212 include a pressure sensor configured to detect a pressure of the interior 128 of the balloon 110. In one embodiment, the system 100 includes a sensor in the form of a flow meter 213 (FIG. 1) that is configured to detect the flow rate of fluid driven by the pump 144. Signals from the one or more sensors 212 are fed via wires or other conventional means to a controller 214 that can use the information received from the sensors 212 to control components of the system 100, such as the pump 144.

Figure 13:
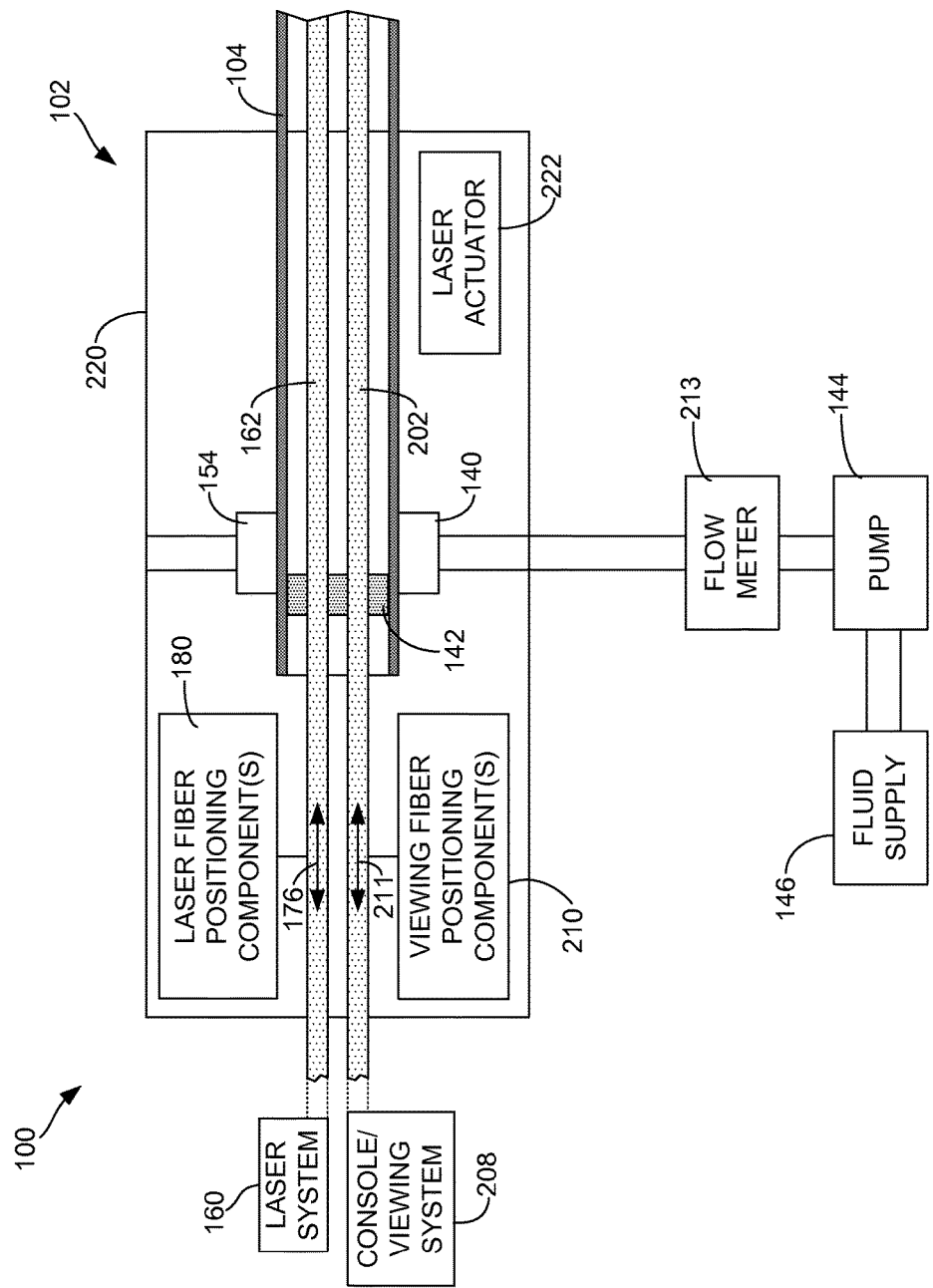
FIG. 13 is a simplified diagram of the applicator including a handheld unit in accordance with embodiments of the invention.

One embodiment of the applicator 102 comprises a handheld unit 220, an exemplary embodiment of which is illustrated in FIG. 13. The handheld unit 220 is generally configured to support components of the applicator 102 described above. In one embodiment, the unit 220 is configured to support the proximal end 106 of the shaft 104. In one embodiment, the unit 220 is configured to support the laser fiber 162. In accordance with other embodiments, the handheld unit 220 is configured to support the viewing fiber 202, the one or more laser fiber positioning components 180 and/or the one or more viewing fiber positioning components 210 described above. In accordance with another embodiment, the handheld unit 220 is configured to receive tubing 250 used to pump fluid or gas through the shaft 104 and into the balloon 110.

In one embodiment, the handheld unit 220 allows the laser fiber 162 to pass through the body of the unit 220 for attachment to the laser system 160. Similarly, the handheld unit 220 allows for the viewing fiber 202 to pass through the body of the unit 220 for coupling to the viewing system 208.

In one embodiment, the handheld unit 220 supports a laser actuator 222 that is configured to trigger the laser system 160 to deliver laser energy down the laser fiber 162 to the distal end 168. Embodiments of the laser actuator 222 include a button, a finger trigger, or other suitable mechanism. One embodiment of the laser actuator 222 that is not supported by the handheld unit 220 is a foot-activated switch.

Figure 14:
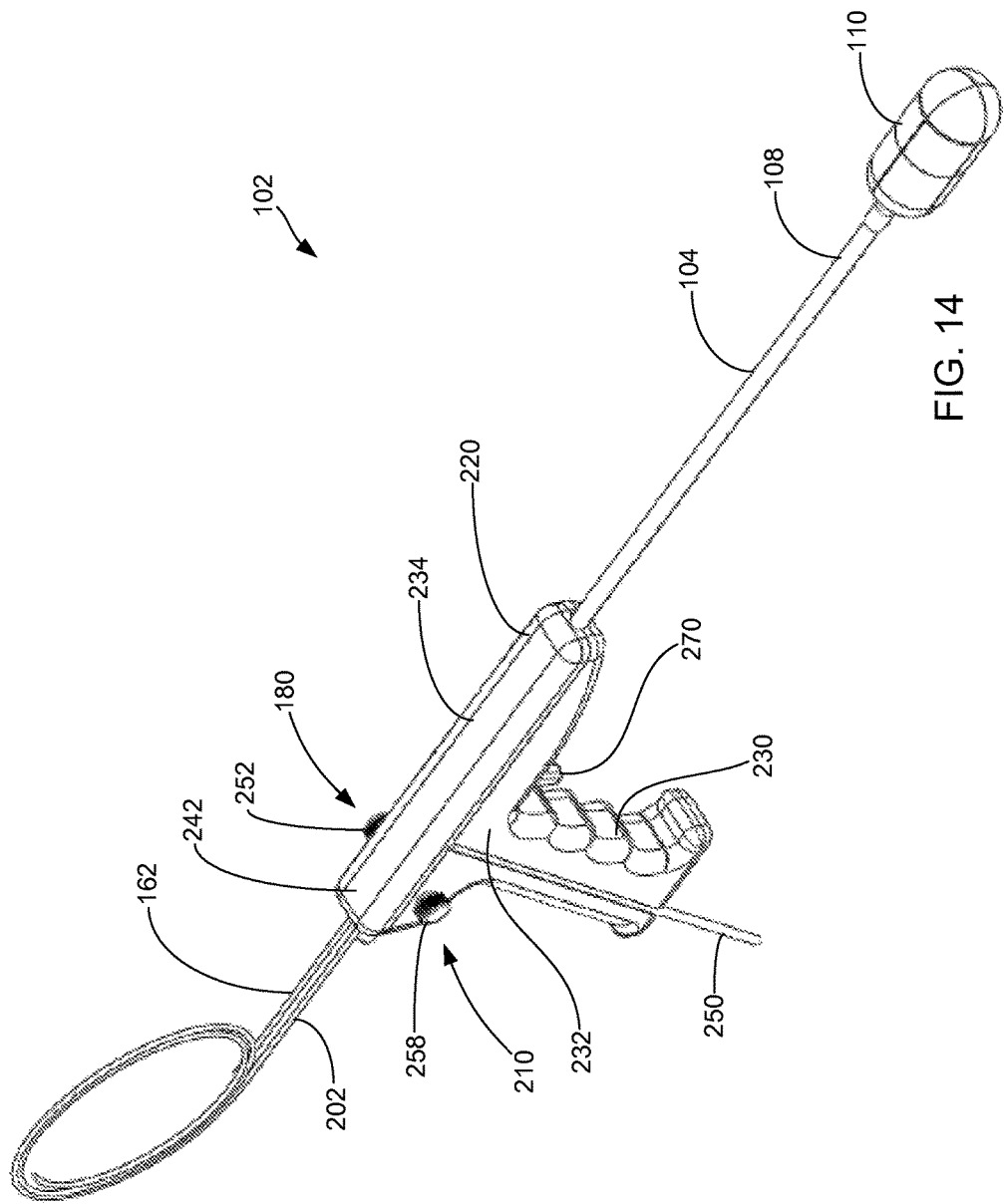
FIGS. 14-16 respectively show isometric assembled, isometric exploded and magnified isometric views of the applicator with a handheld unit formed in accordance with exemplary embodiments of the invention.
Figure 15:
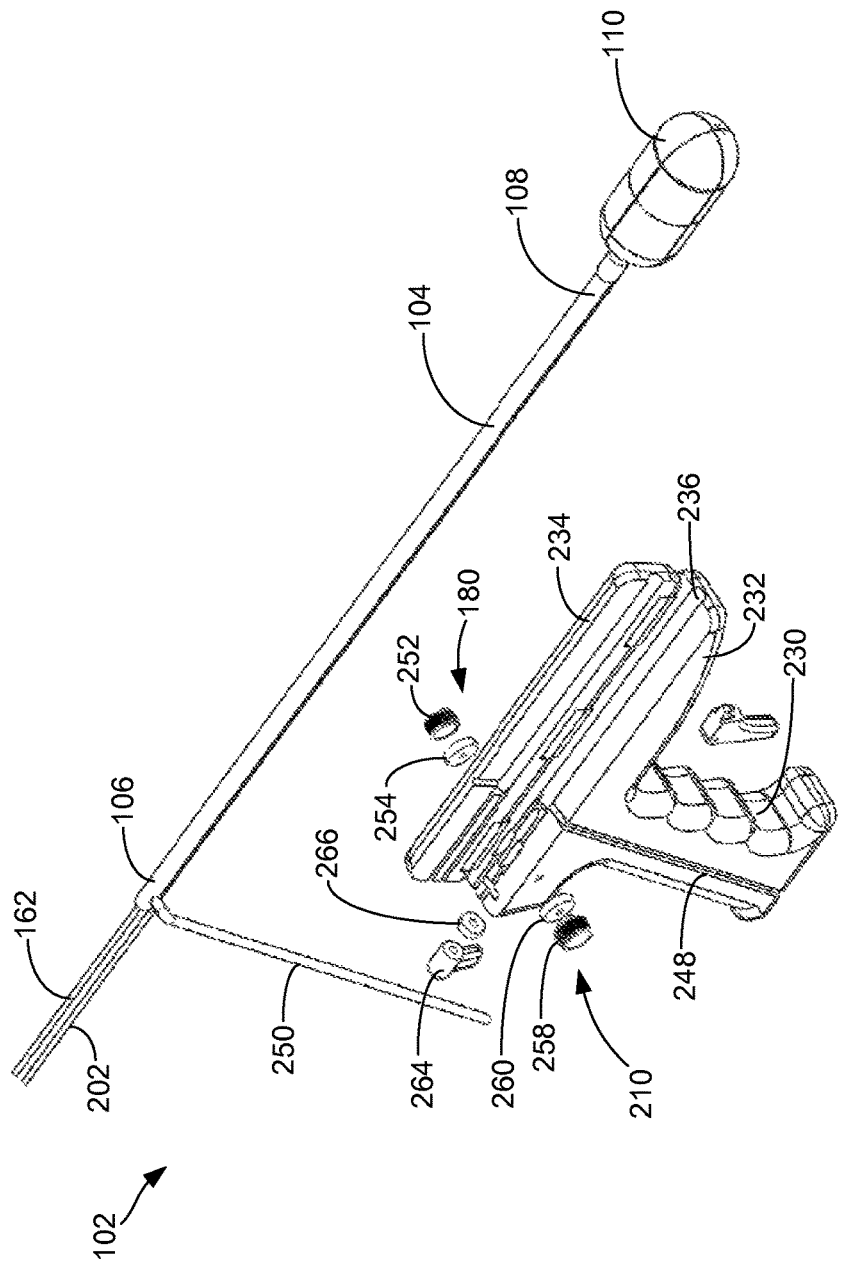
Figure 16:
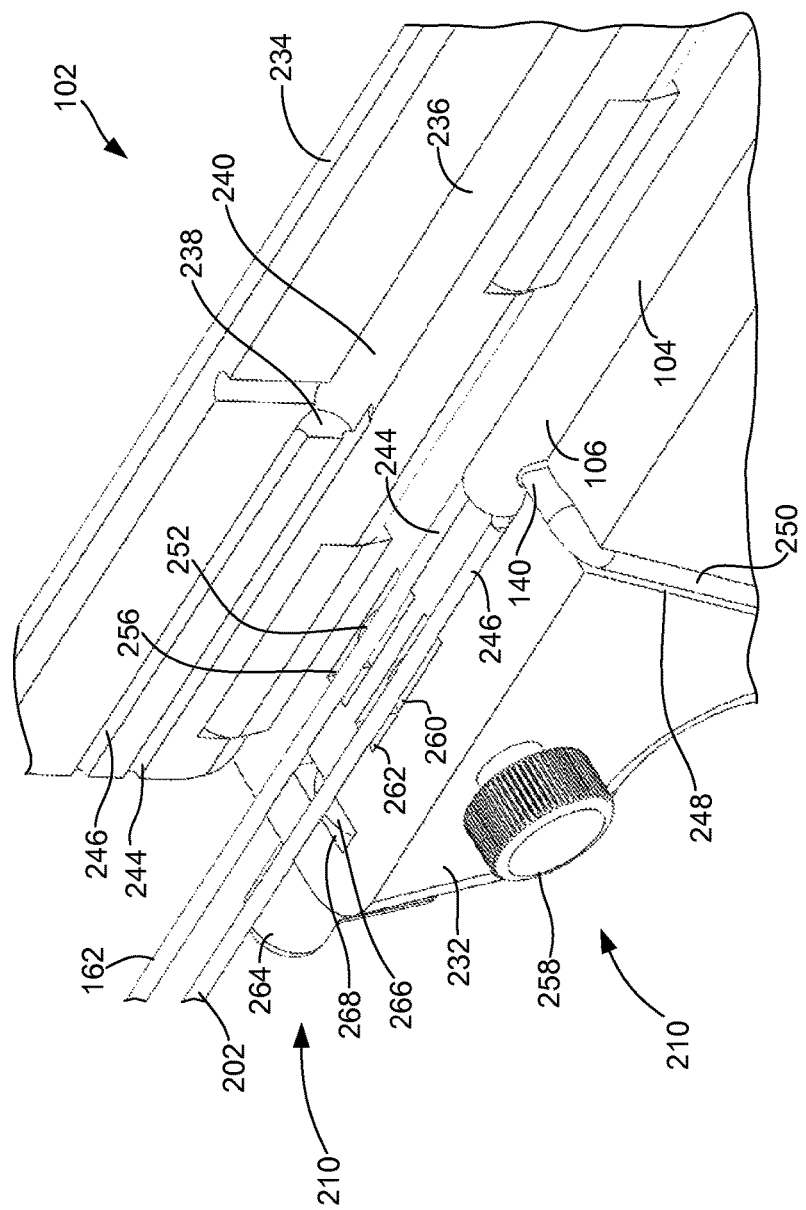

FIGS. 14-16 respectively show isometric assembled, isometric exploded and magnified isometric views of the applicator 102 with a handheld unit 220 formed in accordance with exemplary embodiments of the invention. In one embodiment, the handheld unit 220 comprises a pistol grip 230 and a support member 232 that extends transversely to the pistol grip 230. In one embodiment, the support 232 comprises a hinged cover 234 having a closed position (FIG. 14) and an opened position (FIG. 15). A bore 236 is formed in the support 232 and/or the cover 234 and is sized to receive the shaft 104, as shown in FIG. 16. In one embodiment, the shaft 104 is securely held within the bore 236 when the cover 234 is in the closed position such that inadvertent movement of the shaft 104 in the longitudinal direction during normal handling of the applicator 102 is prevented. In one embodiment, the support 232 and/or the cover 234 includes a shoulder portion 238 at a proximal end 240 of the bore 236 that prevents the shaft 104 from sliding toward the rear 242 of the support 232 along the longitudinal axis.

In one embodiment, the support 232 and/or the cover 234 comprise a channel 244 that is configured to receive the laser fiber 162, as best shown in FIG. 16. The channel 244 extends to the shoulder portion 238 where it receives the laser fiber 162 where it exits the shaft 104. The channel 244 extends from the shoulder 238 out the rear end of the support 232 where it can be coupled to the laser system 160 in a conventional manner.

Another embodiment of the handheld unit 220 comprises a channel 246 formed in the support 232 and/or the cover 234, as best shown in FIG. 16. The channel 246 extends from the shoulder portion 238 out the rear end 242 of the support 232. The channel 246 is configured to receive the viewing fiber 220 as it exits the proximal end 106 of the shaft 104 and allows the viewing fiber 202 to extend out the rear end 242 of the support member 232 where it can be connected to the viewing system 208.

In one embodiment, the handheld unit 220 includes a channel 248 configured to receive conduit 250 that is coupled to the fluid input port 140, as shown in FIG. 16. In one embodiment, the channel 248 extends through the support 232 and the pistol grip 230. The exposed end of the conduit 250 may be coupled to the flow meter 213 or pump 144 using conventional means.

As discussed above, one embodiment of the handheld unit 220 includes the one or more laser fiber positioning components 180. In one embodiment, the laser fiber positioning components 180 comprise a thumb wheel 252 that is coupled to a roller 252 through a gear, axle, or other suitable arrangement, as shown in FIG. 15. The roller 252 engages the laser fiber 162 through a slot 256 in the support 232, as shown in FIG. 16. One embodiment of the roller 252 comprises an exterior surface that comprises rubber or other suitable material that provides sufficient frictional resistance with the exterior of the laser fiber 162 to grip the laser fiber 162 and inhibit sliding contact between the roller 254 and the laser fiber 162. Rotation of the thumb wheel 252 rotates the roller 254, which drives the longitudinal movement of the laser fiber 162 in either the forward or rearward direction relative to the handheld unit 220 and the shaft 104. Thus, one may move the distal end 168 of the laser fiber 162 relative to the balloon 110 to position the distal end 168 as desired.

One embodiment of the one or more viewing fiber positioning components 210 includes a thumb wheel 258 and a roller 260 that operate similarly to the thumb wheel 252 and roller 254 described above to move the viewing fiber 202 in the longitudinal direction relative to the handheld unit 220, the shaft 104 and the balloon 110. The thumb wheel 258 is coupled to the roller 260 through a suitable arrangement, such as a gear. The roller 260 is exposed to engage the viewing fiber 202 through a slot 262 in the support 232. The roller 260 comprises an exterior surface that is formed of a material (e.g., rubber) that generates sufficient frictional resistance with the viewing fiber 202 to inhibit sliding contact between the roller 260 and the viewing fiber 202 as the roller 260 is rotated. Rotation of the thumb wheel 258 causes the roller 260 to rotate, which drives the viewing fiber in the longitudinal direction relative to the handheld unit 220, the shaft 104 and the balloon 110. Thus, the longitudinal position of the distal end 204 of the viewing fiber 202 can be positioned as desired relative to the balloon 110 using the thumb wheel 258.

Another embodiment of the handheld unit 220 comprises one or more viewing fiber positioning components 210 that are configured to rotate the viewing fiber 202 about its longitudinal axis. One embodiment of the components 210 comprise a rotatable member 264, such as a thumb wheel, and a roller 266. The rotatable member 264 is coupled to the roller 266 through an axle, gear, or other suitable arrangement, such that rotation of the member 264 causes the roller 266 to rotate. In one embodiment, the axes of rotation of the member 264 and the roller 266 are parallel to the longitudinal axis of the viewing fiber 202 and the channel 246. The roller 266 engages the viewing fiber 202 through a slot 268. The exterior surface of the roller 266 is formed of a material (e.g., rubber) that produces sufficient frictional resistance with the viewing fiber 202 to inhibit sliding contact with the viewing fiber 202 as the roller 266 rotates. The rotation of the member 264 causes the roller 266 to rotate, which drives the rotation of the viewing fiber 202 about its longitudinal axis. This allows the distal end 204 of the viewing fiber 202 to be rotated as desired within the balloon 110. One embodiment of the one or more laser fiber positioning components 180 includes components that are similar to the rotatable member 264 and the roller 266 that can be used to rotate the laser fiber 162 about its longitudinal axis.

In one embodiment, the handheld unit 220 includes the laser actuator 222 in the form of a trigger 270 that is mounted to the support 232. In one embodiment, actuation of the trigger 270 directs the laser system 160 to transmit laser light through the laser fiber 162 for discharge through the dispenser 166.

In one embodiment, the shaft 104, the balloon 110, the laser fiber 162, the viewing fiber 202, the tubing 250, and/or the port 140 form a disposable group of components. In one embodiment, one or more of these components are provided as a kit in sterilized packaging. In one embodiment, one or more of these components come pre-assembled. For instance, a disposable assembly may comprise the shaft 104, the balloon 110, the laser fiber 162 and the tubing, as shown in FIG. 15, that is ready for installation within the handheld unit 220. One or more of the other components described above, such as the seal 142, may also be included the disposable assembly.

Additional embodiments of the invention include methods of ablating tissue of a patient, or performing another laser treatment, using the system 100. In one embodiment of the method, the system 100 formed in accordance with one or more embodiments described above is provided and the system is prepared for the ablation operation. This may involve the providing of the disposable assembly described above in, for example, sterilized packaging. The disposable assembly is then installed in the handheld unit 202.

In one embodiment, the laser fiber 162 is connected to the laser system 160. In one embodiment, the viewing fiber 202 (if present) is connected to the viewing console 208. In one embodiment, the tubing 250 is fluidically coupled to the pump 144. In one embodiment, connections are made between the one or more sensors 212 and the controller 214.

In one embodiment, a coating, such as an adjuvant, is applied to the exterior surface of the balloon 110, which is placed in contact with the target tissue when the balloon 110 is inflated within the cavity of the patient. The adjuvant is designed to enhance laser tissue ablation by absorbing the wavelength of laser light that will be applied to the tissue. Embodiments of the coating are described in U.S. patent application Ser. No. 12/468,668 filed May 19, 2009 entitled "ADJUVANT ENHANCED ABLATION," which is incorporated herein by reference in its entirety.

In one embodiment, the balloon 110 is placed in the deflated state 124 and the distal end 108 of the shaft 104 is fed into the cavity of the patent, such as the uterus, where the target tissue is located. In one embodiment, the cavity is visually inspected using the viewing fiber 202.

In one embodiment, the balloon 110 is inflated within the cavity by pumping either fluid or gas through the tubing 250 and the port 140, such as using the pump 144. In one embodiment, the inflated state 126 of the balloon engages the interior wall of the cavity, such as illustrated in FIG. 5.

In one embodiment, the cavity and the inflated balloon 110 are inspected using the viewing fiber 202. This involves moving the distal end 204 of the viewing fiber 202 axially and/or angularly using the one or more viewing fiber positioning components 210.

In one embodiment, the markings 139 on the balloon are imaged or viewed using the viewing fiber 202. The markings indicate whether the balloon 110 is properly inflated and/or positioned within the cavity of the patient. In one embodiment, the balloon 110 is deflated, repositioned and inflated again until the markings 139 indicate that the balloon 110 is fully inflated and/or in the desired position within the cavity.

In one embodiment, the laser fiber 162 is positioned as desired relative to the shaft 104 and the balloon 110 using the one or more laser fiber positioning components 180. This may involve moving the distal end 168 axially, angularly, or along an arc.

In one embodiment, the laser system 160 is activated to transmit laser light 164 through the laser fiber 162 and out the dispenser 166 to ablate the targeted tissue. In one embodiment, this activation of the laser system is responsive to the actuation of the laser actuator 222. In one embodiment, the targeted tissues are inspected using the viewing fiber 202.

In one embodiment, the dispenser 166, the distal end 108 of the shaft 104, and/or the balloon 110 are configured to provide substantially uniform transmission of the laser light 164.

In one embodiment, the dispenser 166, the distal end 108 of the shaft 104, and/or the balloon 110 are configured to provide non-uniform transmission of the laser light to control the exposure of the target tissue to the laser light. In one embodiment, a coating is applied to the shaft 104 and/or the interior of the balloon 110 to control the transmission of the laser light therethrough.

In one embodiment, the distal end 168 of the laser fiber 162 is moved along an arc and/or axially to another position relative to the shaft 104 and the balloon 110 to target other tissue within the cavity of the patient.

In one embodiment, a flow of fluid or gas is circulated through the balloon 110. In one embodiment, the flow of fluid or gas is regulated responsive to a temperature signal from a temperature sensor 212.

Following the completion of the ablation treatment, the balloon 110 is returned to its deflated state 124 and the balloon 110, the shaft 104, the laser fiber 162 and other components of the system (e.g., the viewing fiber 202) are removed from the cavity. The disposable components can then be detached from the laser system 160, the pump 144 and the viewing console 208, removed from the applicator 102 and discarded.

Although the present invention has been described with reference to preferred embodiments, workers skilled in the art will recognize that changes may be made in form and detail without departing from the spirit and scope of the invention.

What is claimed is:

1. An applicator comprising:
   a shaft with a proximal end opposite of a distal end along a longitudinal axis;
   a balloon attached to the distal end of the shaft, wherein the balloon comprises a first balloon attached to the distal end of the shaft, the distal end of the shaft being within the first balloon and a second balloon within the first balloon, the second balloon being formed of a material that is less distensible than a material forming the first balloon;
   a support attached to a proximal end of the shaft;
   a plurality of channels extending through each of the support and the shaft in a direction parallel with the longitudinal axis; and
   at least one positioning component that is mounted on the support and operable to move a fiber placed in one of the plurality of channels.

2. The applicator of claim 1, wherein the fiber is a laser fiber.

3. The applicator of claim 2, wherein the support includes a laser actuator that is operable with a laser source to deliver laser light with the laser fiber.

4. The applicator of claim 1, wherein the support is removably attached to the proximal end of the shaft.

5. The applicator of claim 4, further including a bore extending through the support, wherein the support includes a hinged cover having an open position, wherein the proximal end of the shaft is removable from the bore, and a closed position, wherein the proximal end of the shaft is attached to the bore.

6. The applicator of claim 1, further including a bore extending through the support along a longitudinal axis of the support from the distal end to an internal point, the bore having an interior surface configured to receive and retain the proximal end of the shaft in the bore, the shaft having a shaft channel extending therethrough;

wherein at least one of the plurality of channels is formed by aligning a support channel extending through the support from the proximal end to the internal point, with the shaft channel when the proximal end of the shaft is received in the bore.

7. The applicator of claim 6, wherein the interior surface of the bore has a diameter sized to receive the shaft, and a shoulder positioned to retain the proximal end of the shaft in the bore.

8. The applicator of claim 7, wherein the support includes a hinged cover having an open position, wherein the proximal end of the shaft is receivable in the bore, and a closed position, wherein the proximal end of the shaft is retainable in the bore.

9. The applicator of claim 8, wherein the proximal end of the shaft has a fluid input port, and the support further includes a conduit channel leading to the fluid input port.

10. The applicator of claim 9, wherein the support includes a grip extending transversely to the longitudinal axis, and the conduit channel extends through the grip.

11. The applicator of claim 6, wherein the at least one positioning component includes a first wheel, and rotation of the first wheel causes movement of the fiber.

12. The applicator of claim 11, further comprising an axle extending through the support along a lateral axis transverse with the longitudinal axis, wherein the first wheel is coupled to a first roller and the axle, an exterior surface of the first roller is engageable with an exterior surface of the first fiber, and rotation of the first wheel about the lateral axis causes translational movement of the fiber along the longitudinal axis.

13. The applicator of claim 11, wherein the rotation of the first wheel causes translational movement of the fiber along the longitudinal axis, the positioning component further includes a second wheel, and rotation of the second wheel causes rotational movement of the fiber about the longitudinal axis.

* * * * *